(12) United States Patent
Cummins

(10) Patent No.: US 7,008,435 B2
(45) Date of Patent: Mar. 7, 2006

(54) SURGICAL STAPLING DEVICE AND METHOD

(76) Inventor: Christy Cummins, 9 Furnes Manor, Johnstown, Naas, County Kildare (IE)

( * ) Notice: Subject to any disclaimer, the term of this patent is extended or adjusted under 35 U.S.C. 154(b) by 14 days.

(21) Appl. No.: 10/486,070

(22) PCT Filed: Aug. 8, 2002

(86) PCT No.: PCT/IE02/00118

§ 371 (c)(1),
(2), (4) Date: Feb. 6, 2004

(87) PCT Pub. No.: WO03/013363

PCT Pub. Date: Feb. 20, 2003

(65) Prior Publication Data

US 2004/0249391 A1 Dec. 9, 2004

(30) Foreign Application Priority Data

Aug. 9, 2001 (IE) ................................ S2001/0748

(51) Int. Cl.
*A61B 17/10* (2006.01)
(52) U.S. Cl. .................. 606/139; 606/143; 606/219; 606/220
(58) Field of Classification Search ............... 606/139, 606/142, 143, 151, 219, 220, 75, 213, 215; 411/457, 458, 469, 473, 474, 480, 481; 604/116; 227/175.01–182.1
See application file for complete search history.

(56) References Cited

U.S. PATENT DOCUMENTS

| | | | | |
|---|---|---|---|---|
| 1,088,393 A | * | 2/1914 | Backus | 24/103 |
| 1,331,401 A | * | 2/1920 | Summers | 24/94 |
| 2,087,074 A | * | 7/1937 | Tucker | 24/113 MP |
| 2,453,227 A | * | 11/1948 | Janes | 24/95 |
| 2,944,311 A | * | 7/1960 | Schneckenberger | 24/104 |
| 3,142,878 A | * | 8/1964 | Santora | 24/96 |
| 3,482,428 A | | 12/1969 | Kapitanov et al. | |
| 4,014,492 A | | 3/1977 | Rothfuss | |

(Continued)

FOREIGN PATENT DOCUMENTS

EP     0 386 361     9/1990

(Continued)

*Primary Examiner*—Anhtuan T. Nguyen
*Assistant Examiner*—Michael Mendoza
(74) *Attorney, Agent, or Firm*—Nutter, McClennen & Fish LLP

(57) ABSTRACT

A surgical stapling device is provided having an elongate housing and a surgical staple slidable longitudinally within the housing towards a free forward end thereof, the staple having a back and two forwardly pointing legs. The housing contains a staple-firing mechanism for driving the staple towards the free end of the housing, bending the staple to bring the free ends of the legs towards one another to close the staple, and releasing the closed staple. A cap is located at the free end of the housing at a position where, in operation of the staple-firing mechanism, the cap becomes trapped between the back of the closed staple and human or animal tissue being stapled so as to provide a greater area of pressure on the tissue than in the absence of the cap.

8 Claims, 4 Drawing Sheets

U.S. PATENT DOCUMENTS

| | | |
|---|---|---|
| 4,278,091 A | 7/1981 | Borzone |
| 4,523,695 A | 6/1985 | Braun et al. |
| 4,724,840 A | 2/1988 | McVay et al. |
| 4,771,782 A | 9/1988 | Millar |
| 4,789,090 A | 12/1988 | Blake, III |
| 4,934,364 A | 6/1990 | Green |
| 5,108,421 A | 4/1992 | Fowler |
| 5,131,379 A | 7/1992 | Sewell, Jr. |
| 5,147,381 A | 9/1992 | Heimerl et al. |
| 5,192,300 A | 3/1993 | Fowler |
| 5,209,756 A * | 5/1993 | Seedhom et al. ............ 606/151 |
| 5,275,616 A | 1/1994 | Fowler |
| 5,292,309 A | 3/1994 | Van Tassel et al. |
| 5,292,332 A | 3/1994 | Lee |
| 5,306,254 A | 4/1994 | Nash et al. |
| 5,352,229 A | 10/1994 | Goble et al. |
| 5,395,030 A | 3/1995 | Kuramoto et al. |
| 5,431,639 A | 7/1995 | Shaw |
| 5,443,481 A | 8/1995 | Lee |
| 5,470,010 A | 11/1995 | Rothfuss et al. |
| 5,478,352 A | 12/1995 | Fowler |
| 5,527,322 A | 6/1996 | Klein et al. |
| 5,536,251 A | 7/1996 | Evard et al. |
| 5,560,532 A | 10/1996 | DeFonzo et al. |
| 5,591,205 A | 1/1997 | Fowler |
| 5,601,602 A | 2/1997 | Fowler |
| 5,620,461 A | 4/1997 | Muijs Van De Moer et al. |
| 5,643,318 A | 7/1997 | Tsukernik et al. |
| 5,645,566 A | 7/1997 | Brenneman et al. |
| 5,674,231 A | 10/1997 | Green et al. |
| 5,676,689 A | 10/1997 | Kensey et al. |
| 5,716,375 A | 2/1998 | Fowler |
| 5,810,846 A | 9/1998 | Virnich et al. |
| 5,855,312 A | 1/1999 | Toledano |
| 5,861,005 A | 1/1999 | Kontos |
| 6,004,341 A | 12/1999 | Zhu et al. |
| 6,007,563 A | 12/1999 | Nash et al. |
| 6,022,372 A | 2/2000 | Kontos |
| 6,048,358 A | 4/2000 | Barak |
| 6,056,768 A | 5/2000 | Cates et al. |
| 6,090,130 A | 7/2000 | Nash et al. |
| 6,197,042 B1 | 3/2001 | Ginn et al. |
| 6,277,140 B1 | 8/2001 | Ginn et al. |
| 6,305,891 B1 * | 10/2001 | Burlingame ................ 411/469 |
| 6,322,580 B1 | 11/2001 | Kanner |
| 6,348,064 B1 | 2/2002 | Kanner |
| 6,506,210 B1 | 1/2003 | Kanner |
| 6,533,762 B1 | 3/2003 | Kanner et al. |
| 6,623,510 B1 | 9/2003 | Carley et al. |
| 6,634,537 B1 * | 10/2003 | Chen ........................ 227/140 |
| 6,719,777 B1 | 4/2004 | Ginn et al. |
| 6,755,842 B1 | 6/2004 | Kanner et al. |
| 6,767,356 B1 | 7/2004 | Kanner et al. |
| 2002/0049427 A1 | 4/2002 | Coleman |
| 2002/0151921 A1 | 10/2002 | Kanner et al. |
| 2003/0097140 A1 | 5/2003 | Kanner |
| 2003/0109890 A1 | 6/2003 | Kanner et al. |
| 2004/0010285 A1 | 1/2004 | Carley et al. |
| 2004/0254591 A1 | 12/2004 | Kanner et al. |
| 2004/0267312 A1 | 12/2004 | Kanner et al. |

FOREIGN PATENT DOCUMENTS

| | | |
|---|---|---|
| EP | 0 534 696 | 3/1993 |
| EP | 0 756 851 | 2/1997 |
| EP | 0 774 237 | 5/1997 |
| EP | 0 941 697 | 9/1999 |
| FR | 2 443 238 | 7/1980 |
| GB | 1 358 466 | 7/1974 |
| WO | WO 97/20505 | 6/1997 |
| WO | WO 98/17179 | 4/1998 |
| WO | WO 98/25508 | 6/1998 |
| WO | WO 00/56227 | 9/2000 |

* cited by examiner (a)

(b)

(a)

(b)

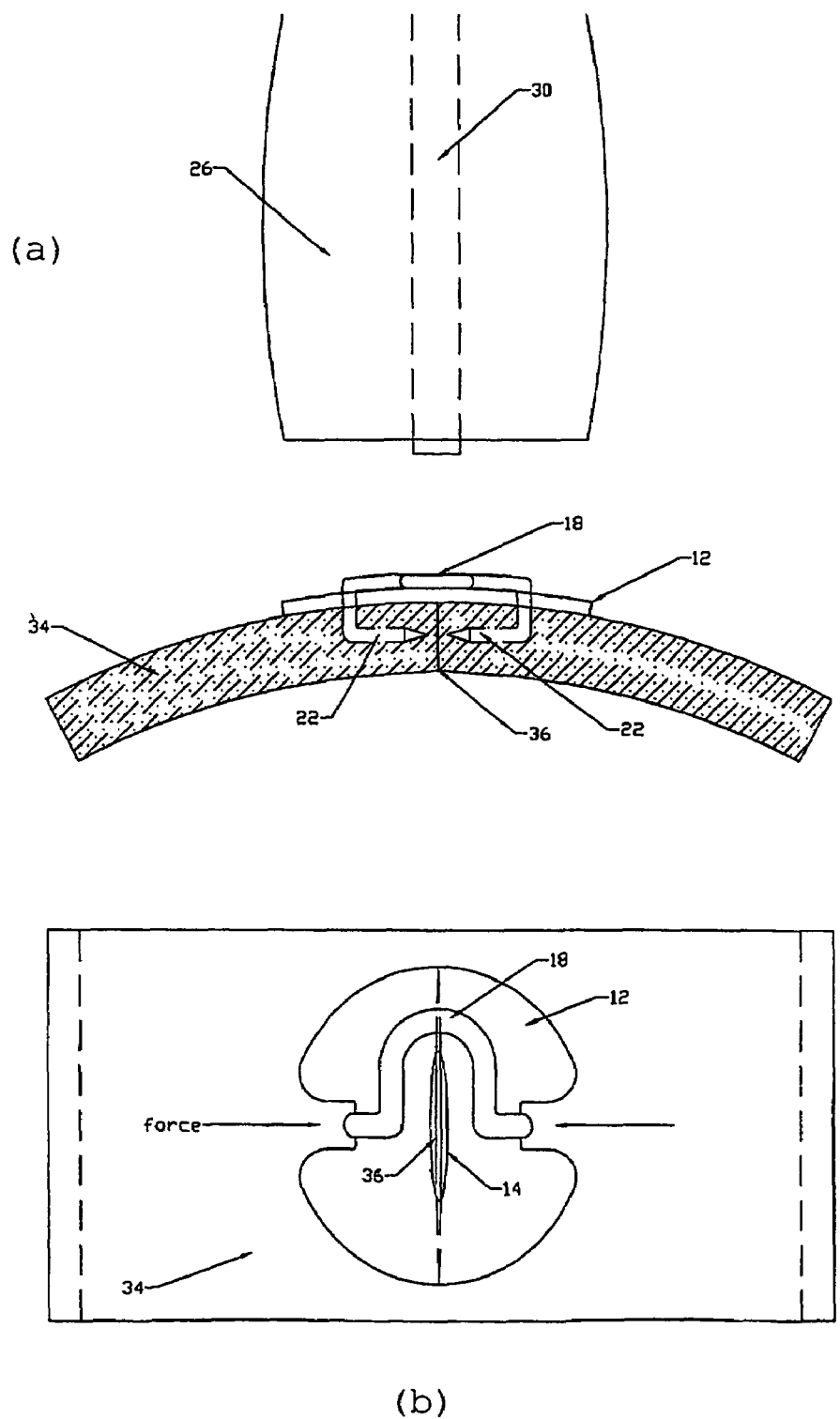

SURGICAL STAPLING DEVICE AND METHOD

CROSS-REFERENCE TO RELATED APPLICATIONS

This application is a continuation application of International Application No. PCT/IE02/00118, filed Aug. 8, 2002, entitled "Surgical Stapling Device and Method," which designated the United States and was published in the English language, and which claims priority to Ireland Application No. 010748, filed Aug. 9, 2001, entitled "Surgical Stapling Device and Methods." These applications are expressly incorporated by reference herein.

This invention relates to a surgical stapling device and method of surgical stapling.

BACKGROUND OF THE INVENTION

When performing catheterisation procedures, such as angiography or angioplasty, a catheter is generally introduced into the vascular system by first penetrating the skin, underlying tissues and blood vessel with a sharpened hollow needle. Next, a guidewire is commonly inserted through the lumen of the hollow needle and is caused to enter the selected blood vessel. Subsequently the needle is typically stripped off the guidewire and the combination of a dilator and/or introducer are fed over the guidewire and pushed through the skin to enter the blood vessel. The guidewire can then be removed and the desired catheter to carry out the procedure is fed through the lumen of the introducer and advanced through the vascular system until the working end of the catheter is appropriately positioned. Following the conclusion of the catheterisation procedure the working catheter will be withdrawn and subsequently the dilator and/or introducer will also be removed from the wound. Following this procedure the vessel puncture must be closed in order to prevent loss of blood through the puncture hole.

Typically the wound is closed by maintaining external pressure over the vessel until the puncture naturally seals. This procedure can take approximately 30 minutes with the length of time usually being greater if the patient is hypertensive or anticoagulated. The procedure can also be uncomfortable for the patient and involves costly professional time on the part of the hospital staff. Other pressure techniques such as pressure bandages, sand bags or clamps have been employed but these also involve ensuring the patient remains motionless for the extended period of time and is monitored to ensure the effectiveness of the procedure.

Therefore there is a need for a device which will close and seal the arterial puncture quickly and easily allowing the patient to become mobile within a short period of time, thereby increasing the throughput of patients in the catheterisation lab and increasing the availability of hospital staff for other duties.

SUMMARY OF THE INVENTION

Accordingly, the invention provides a surgical stapling device comprising an elongate housing, a surgical staple slidable longitudinally within the housing towards a free forward end thereof, the staple having a back and two forwardly pointing legs, a staple-firing mechanism for driving the staple towards the free end of the housing, bending the staple to bring the free ends of the legs towards one another to close the staple, and releasing the closed staple, the stapling device further including a cap located at the free end of the housing at a position where, in operation of the staple-firing mechanism, the cap becomes trapped between the back of the closed staple and human or animal tissue being stapled so as to provide a greater area of pressure on the tissue than in the absence of the cap.

Preferably the device further includes an elongated locator member slidable longitudinally within the housing between an initial forward position wherein the locator member projects beyond the free end of the housing to enter a puncture site in a liquid-carrying vessel in a human or animal, thereby to locate the free end of the housing at the puncture site, and a rearward position wherein the locator member is retracted into the housing in coordination with the closure of the staple, wherein the cap has a central opening which fits over the projecting locator member in its initial forward position, the locator member being withdrawn from the central opening when it is retracted into the housing.

Most preferably the closure of the staple effects a lateral compression of the cap to at least partially close the central opening.

The invention further provides a method of stapling human or animal tissue, the method including providing a stapling device comprising an elongate housing, a surgical staple slidable longitudinally within the housing towards a free forward end thereof, the staple having a back and two forwardly pointing legs, and a staple-firing mechanism for driving the staple towards the free end of the housing, bending the staple to bring the free ends of the legs towards one another to close the staple, and releasing the closed staple, the method further including placing a cap at the free end of the housing and operating the staple-firing mechanism, the cap being located at a position where, in operation of the staple-firing mechanism, the cap becomes trapped between the back of the closed staple and human or animal tissue being stapled so as to provide a greater area of pressure on the tissue than in the absence of the cap.

A preferred embodiment of the invention to be described with reference to the drawings comprises a surgical stapling device as described in Irish Patent Application S2000/0722 in combination with a disk-like cap. The stapling device comprises a handle from which extends an elongated housing (shaft). At its end remote from the handle the shaft terminates in a bullet-like head from which, in an initial "pre-fire" position of the device, a locator tube extends a predetermined distance. A surgical staple with forwardly pointing legs is located wholly within the head of the shaft in the pre-fire position. A generally circular disk having a central opening is positioned over the locator tube concentric with and flush against the head of the shaft. The diameter of the disk is equal to or less than the diameter of the head of the shaft. On each side of the disk generally U-shaped slots are positioned to allow the staple legs to pass through the disk when they are advanced forward during deployment of the staple.

The locator tube locates the head of the shaft centrally over the puncture hole. On activation of the staple firing mechanism the staple is advanced forward so that the legs stab the vessel wall. As the firing cycle continues the locator tube is retracted back into the head of the device and the staple legs are deformed through 90° in order to form a generally rectangular shape. Forming the staple causes the disk to become trapped between the staple back and vessel wall with additional lateral compression of the two side slots so as to close the central opening by which the disk was positioned on the locator tube.

The staple and cap combination has the effect of bringing the two sides of the central opening together and also creating a tamponade effect over an increased surface area so as to bring about haemostasis in a short time.

BRIEF DESCRIPTION OF THE DRAWINGS

An embodiment of the invention will now be described, by way of example, with reference to the accompanying drawings, in which:

FIGS. 4(a) and 4(b), FIGS. 5(a) and 5 (b), and FIGS. 6(a) and 6(b) show successive stages in firing a staple into the wall of a blood vessel using the device of FIG. 2, in which FIGS. 4(a). 5(a) and 6(a) are side elevations of the device and FIGS. 4(b), 5(b) and 6(b) are equivalent plan views of the staple and cap.

DETAILED DESCRIPTION OF THE PRESENT INVENTION

Figure 1:
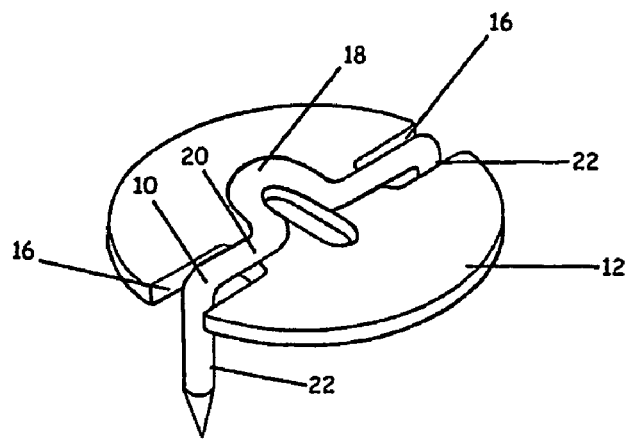
FIG. 1 is a perspective view of a staple and cap combination used in the present embodiment.

FIG. 1 shows a preferred surgical staple 10 and cap or cover 12 for use in the embodiment. The staple 10 is a generally U-shaped staple identical to that described in Irish Patent Application S2000/0722. The cap 12 is a generally circular flat deformable disk with a generally oval central opening 14 and two diametrically opposite generally U-shaped slots 16 extending radially inwardly from the periphery of the disk. The dimensions of the oval opening 14 are substantially the same as the external dimensions of an oval cross-section blood locator tube 30 (FIG. 2), and the major axis of the oval opening 14 is substantially normal to the direction of closure of the staple legs 22.

The disk 12 is constructed from a soft malleable biocompatible metal such as Titanium or a semi-flexible material such as Dacron, Hydrogel, Collagen or Cellulose, or other biocompatible material such as PLA, PGA or PLGA. When the staple 10 is positioned against the disk 12 in use, the hump 18 in the back 20 of the staple is aligned with one half of the oval opening 14 and the staple legs 22 project through the slots 16.

Figure 2:
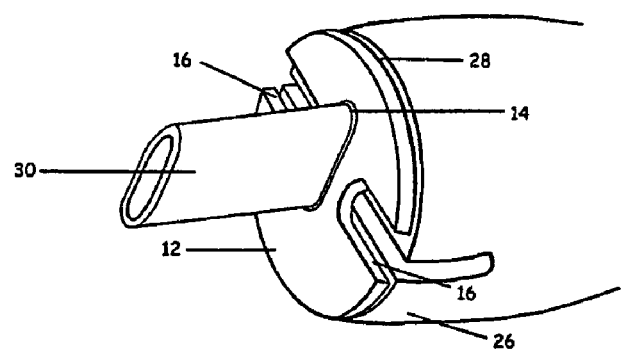
FIG. 2 is a perspective view of the head end of a surgical stapling device according to the present embodiment in a pre-fire position.

FIG. 2 shows a surgical stapling device according to the embodiment of the invention in its "pre-fire" position. Apart from the presence of the disk 12, the device may be identical to that described in Irish Patent Application S2000/0722, from which full details may be obtained. Briefly, however, the device comprises an elongate housing or shaft 24 extending from a pistol-grip type handle (not shown) and terminating in a bullet-like head 26. The staple 10 is slidable longitudinally within the head 26, towards the free forward end 28 of the shaft 24, on a blood locator tube 30 slidable longitudinally within, and initially projecting forwardly beyond, the shaft. The legs 22 of the staple point forwardly. In operation, a trigger on the handle operates a staple-firing mechanism (not shown) within the shaft 24 which drives the staple 10 towards the free end 28, bends the staple to bring the free ends of the legs 22 towards one another to close the staple, and finally releases the closed staple. During this process the blood locator tube 30 is retracted into the housing in coordination with the closure of the staple.

According to the embodiment, the stapling device further includes the disk 12 which is located against the free end 28 of the shaft 24 at a position where, in operation of the staple-firing mechanism, the disk becomes trapped between the humped back 20 of the closed staple and the human or animal tissue being stapled so as to provide a greater area of pressure on the tissue than would be provided by the back 20 of the staple alone.

Figure 3:
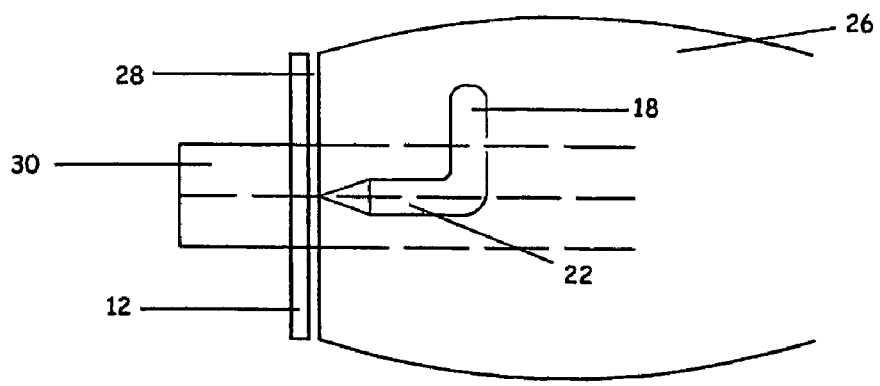
FIG. 3 is a side elevation of stapling device of FIG. 2 in the pre-fire position.

In particular, in the "pre-fire" position of the device, the locator tube 30 extends through the oval opening 14 in the disk 12 and extends a pre-determined distance beyond the free end 28 of the shaft. The staple 10, while positioned further back in the head 26, is in the same general alignment with the disk as shown in FIG. 1. However, it is important that the staple legs 22 are positioned back in the staple head behind the disk 12 and not protruding beyond the free end 28 of the staple head. FIG. 3 is a side elevational view of the stapler head shown in FIG. 2. It can be seen that the staple 10 is positioned across the locator tube 30 and behind the disk 12 at a distance at least equivalent to the length of the staple legs 22.

Figure 4:
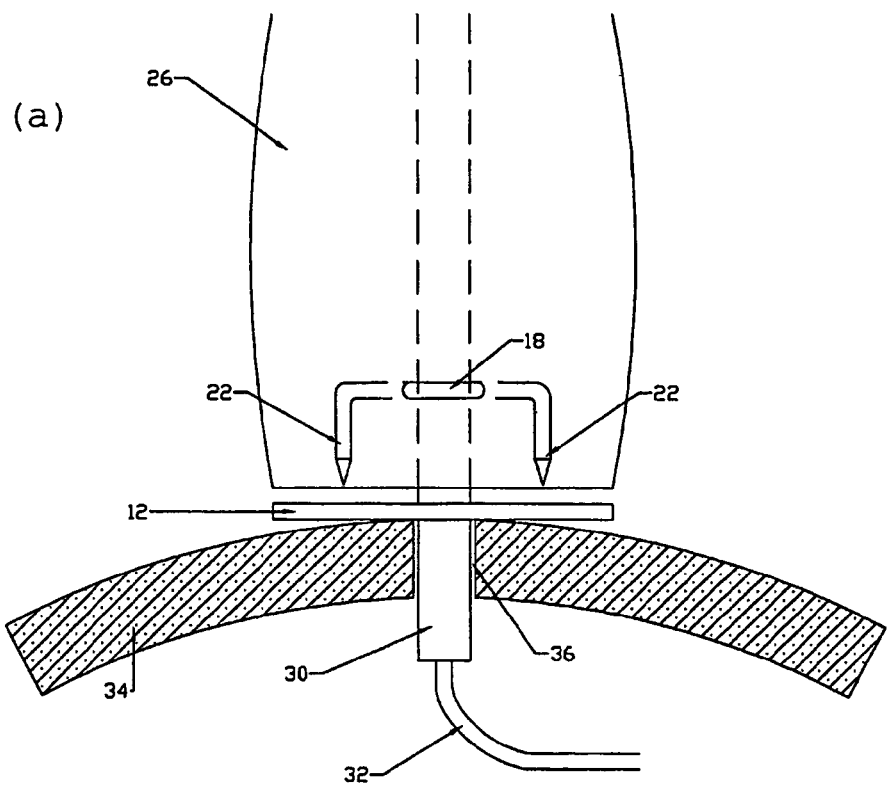
Figure 4:
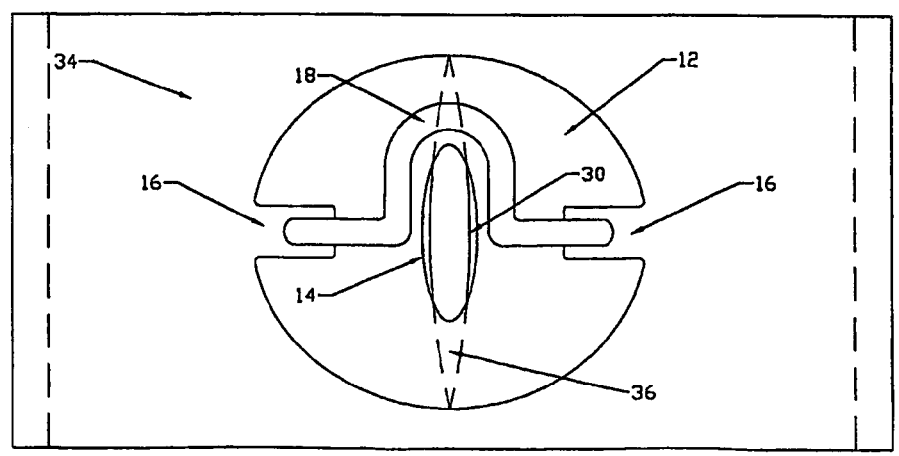
Figure 5:
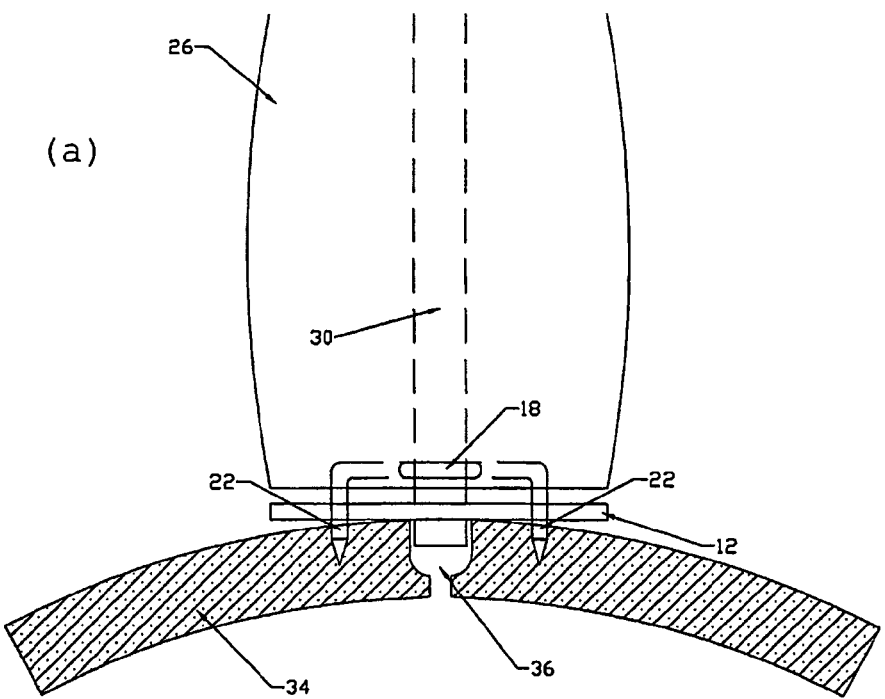
Figure 5:
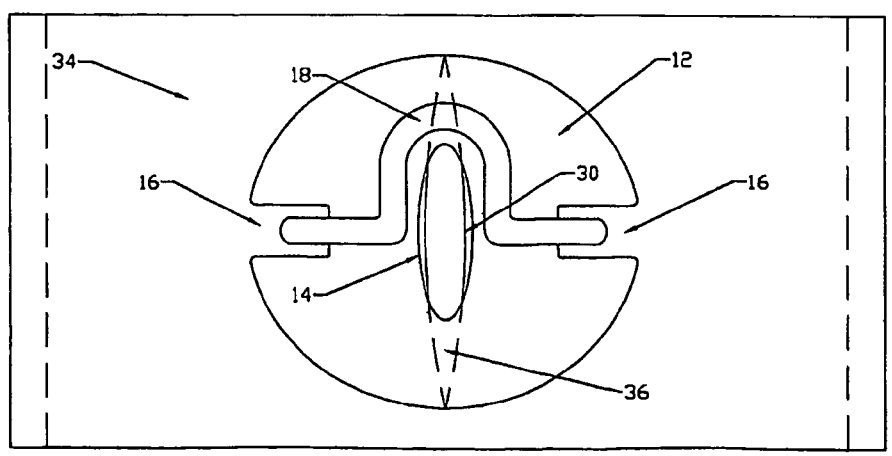

The steps involved in firing the staple 10 and disk 12 are illustrated in FIGS. 4 to 6.

First, FIG. 4(a), the stapler head 26 is tracked over a guidewire 32 through the percutaneous tract until the front end of the locator tube 30 enters a blood vessel 34 providing positive indication that the free end 28 of the shaft 24 is sitting on the outer surface of the vessel adjacent the puncture hole 36 with the staple and disk positioned centrally across the puncture hole (see also FIG. 4(b)).

Now the staple-firing mechanism is operated to drive the staple forwardly such that the staple legs 22 puncture the wall of the vessel 34, FIG. 5(a). At this point the locator tube 30 is also being retracted back into the staple head 26.

Continued operation of the staple-firing mechanism now causes the outer portions of the staple back 20 (i.e. the portions on either side of the hump 18) and the legs 22 to bend through approximately 90° towards one another and close the staple 10 to a generally rectangular configuration, FIG. 4(c). At this point the staple 10 is compressing the cap 12 against the outer surface of the vessel wall thereby closing the puncture hole 36. During the final steps in the deployment process it is important to substantially close the oval opening 14 in the cap to prevent blood from leaking once the staple and cap are deployed. Thus, as seen in FIG. 6(b), as the staple back 20 is deformed, causing the staple legs 22 to arc through 90°, the opposite edges of the disk 12 are compressed inwards causing the central oval opening 14 to close.

An alternative embodiment (not shown) of the disk 12 may, instead of the slots 16, have two diametrically opposite holes which do not extend to the edges of the disk 12. In use these holes are aligned with the staple legs 22 so that the latter project through the holes.

Furthermore, if the disk 12 is made of a resilient material the oval opening 14 may be replaced by a simple slit extending substantially normal to the direction of closure of the staple legs, the slit being resiliently forced apart by insertion of the blood locator tube 30 and closing automatically, by reason of the resilience of the disk, when the tube 30 is retracted. Such an arrangement will not rely on closure of the slit by compression by the staple as the latter is deformed.

The invention is not limited to the embodiments described herein which may be modified or varied without departing from the scope of the invention.

What is claimed is:

1. A surgical stapling device, comprising:
   an elongate housing;
   a surgical staple slidable longitudinally within the housing towards a free forward thereof, the staple having a back and two forwardly pointing legs;
   a staple-firing mechanism for driving the staple towards the free end of the housing, bending the staple to bring the free ends of the legs towards one another to close the staple, and releasing the closed staple; and
   a cap located at the free end of the housing at a position where, in operation of the staple-firing mechanism, the cap becomes trapped between the back of the closed staple and human or animal tissue being stapled so as to provide a greater area of pressure on the tissue than in the absence of the cap, and closure of the staple effects a lateral compression of the cap to at least partially close a central opening formed in the cap.

2. A device as claimed in claim 1, wherein the free end of the housing has a circular cross-section and the cap is generally in the form of a disk positioned substantially concentrically relative to the free end.

3. A device as claimed in claim 2, wherein the disk has two diametrically opposite apertures for accommodating the legs of the staple.

4. A device as claimed in claim 3, wherein the apertures comprise slots extending radially inwards from the periphery of the disk.

5. A device as claimed in claim 1, further including an elongated locator member slidable longitudinally within the housing between an initial forward position wherein the locator member projects beyond the free end of the housing to enter a puncture site in a liquid-carrying vessel in a human or animal, thereby to locate the free end of the housing at the puncture site, and a rearward position wherein to locator member is retracted into the housing in coordination with the closure of the staple, wherein the central opening in the cap fits over the projecting locator member in its initial forward position, the locator member being withdrawn from the central opening when it is retracted into the housing.

6. A device as claimed in claim 5, wherein the disk is made of a resilient material and the central opening is a slit extending substantially normal to the direction of closure of the staple legs, the slit being resiliently forced apart by insertion of the blood locator tube and closing automatically, through the resilience of the disk, when the blood locator tube is retracted.

7. A device as claimed in claim 5, wherein the central opening is generally oval with its major axis substantially normal to the direction of closure of the staple legs.

8. A method of stapling human or animal tissue, the method including:
   providing a stapling device comprising an elongate housing, a surgical staple slidable longitudinally within the housing towards a free forward end thereof, the staple having a back end two forwardly pointing legs, and a staple-firing mechanism for driving the staple towards the free end of the housing;
   bending the staple to bring the free ends of the legs towards one another to close the staple;
   releasing the closed staple; and
   placing a cap at the free end of the housing and operating the staple-firing mechanism, the cap being located at a position where, in operation of the staple-firing mechanism, the cap becomes trapped between the back of the closed staple and human or animal tissue being stapled so as to provide a greater area of pressure on the tissue than in the absence of the cap.

* * * * *